United States Patent [19]

Sallmann et al.

[11] 4,173,577
[45] Nov. 6, 1979

[54] PHENYLACETOHYDROXAMIC ACIDS

[75] Inventors: Alfred Sallmann, Bottmingen; Rudolf Pfister, Basel, both of Switzerland

[73] Assignee: Ciba-Geigy Corporation, Ardsley, N.Y.

[21] Appl. No.: 877,066

[22] Filed: Feb. 13, 1978

Related U.S. Application Data

[60] Division of Ser. No. 665,986, Mar. 11, 1976, Pat. No. 4,092,430, which is a continuation of Ser. No. 467,366, May 6, 1974, abandoned, which is a continuation-in-part of Ser. No. 177,088, Sep. 1, 1971, abandoned.

[30] Foreign Application Priority Data

Sep. 9, 1970 [CH] Switzerland ............ 13415/70
Jul. 16, 1971 [CH] Switzerland ............ 10580/71

[51] Int. Cl.² .................. C07C 83/10; A61K 31/185
[52] U.S. Cl. ...................... 260/500.5 H; 424/315
[58] Field of Search ............. 260/518 A, 500.5 H

[56] References Cited

U.S. PATENT DOCUMENTS

| | | | |
|---|---|---|---|
| 3,586,713 | 6/1971 | Buu-Hoi et al. | 260/500.5 H |
| 3,673,243 | 6/1972 | Yamamoto et al. | 260/518 A |
| 3,681,445 | 8/1972 | Ruyle et al. | 260/500.5 H |
| 3,692,819 | 9/1972 | Carney | 260/500.5 H |
| 3,697,588 | 10/1972 | Vincent et al. | 260/500.5 H |
| 3,821,268 | 6/1974 | Diamond et al. | 260/500.5 H |
| 3,828,093 | 8/1974 | Bays et al. | 260/500.5 H |
| 3,852,323 | 12/1974 | Diamond et al. | 260/500.5 H |

FOREIGN PATENT DOCUMENTS 492679 8/1970 Switzerland ............ 260/518 A

*Primary Examiner*—Joseph E. Evans
*Attorney, Agent, or Firm*—Theodore O. Groeger

[57] ABSTRACT

Phenylacetohydroxamic acids having the formula I

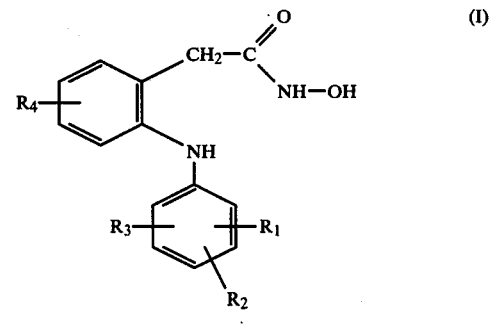

wherein $R_1$, $R_2$, $R_3$ and $R_4$, independently of each other, represent hydrogen, chlorine, fluorine or bromine atoms or an alkyl or alkoxy group having at most 6 carbon atoms, and wherein $R_2$ may additionally represent a trifluoromethyl group with the proviso that $R_1$, $R_2$ and $R_3$ may not simultaneously represent hydrogen atoms and their pharmaceutically acceptable salts with bases, which compounds inhibit plateletaggregation and exhibit valuable pharmacological, in particular, antiphlogistic, analgesic and antipyretic activity.

3 Claims, No Drawings

PHENYLACETOHYDROXAMIC ACIDS

CROSS REFERENCE

This application is a divisional of application Ser. No. 665,986, filed Mar. 11, 1976 (now U.S. Pat. No. 4,092,430), which in turn is a continuation of Ser. No. 467,366, filed May 6, 1974, which in turn is a continuation in part of Ser. No. 177,088 filed Sept. 1, 1971 (both of which are now abandoned).

DETAILED DESCRIPTION

The invention relates to new phenylacetophydroxamic acids and their salts having valuable pharmacological properties, to processes for the production of these substances, to pharmaceutical preparations containing these substances, and to the use of the said preparations.

The invention relates, in particular, to new phenylacetohydroxamic acids of formula I:

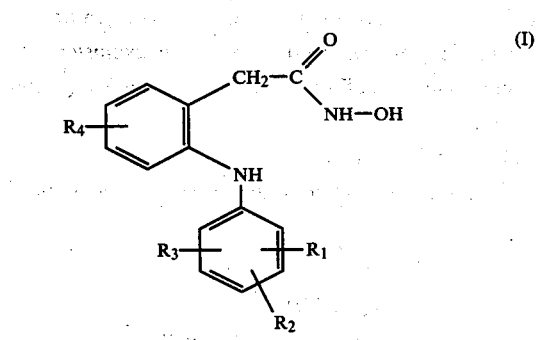

wherein $R_1$ represents hydrogen, lower alkyl, lower alkoxy, or halogen up to and including atomic number 35, $R_2$ represents hydrogen, lower alkyl, lower alkoxy, halogen up to and including atomic number 35, or trifluoromethyl, $R_3$ represents hydrogen, lower alkyl, lower alkoxy, or halogen up to and including atomic number 35, and $R_4$ represents hydrogen, lower alkyl, lower alkoxy, or halogen up to and including atomic number 35, with exclusion of the simultaneous definition of the substituents $R_1$, $R_2$ and $R_3$ as hydrogen, to salts thereof, as well as to processes for the production of these substances.

In the following, the expression 'lower' in connection with alkyl radicals and groups derived from these radicals is used to denote such radicals which contain up to 6, but preferably 1 to 3, carbon atoms.

Lower alkyl radicals are, e.g. methyl, ethyl, propyl, isopropyl radicals, or straight or branched butyl, pentyl or hexyl radicals in any desired position.

Lower alkoxy radicals are, e.g. methoxy, ethoxy, propoxy, isopropoxy, butoxy, pentyloxy and hexyloxy groups.

As lower alkyl, the substituents $R_1$, $R_2$, $R_3$ and $R_4$ are preferably an alkyl group having 1 to 2 carbon atoms, e.g. the methyl or ethyl group.

As lower alkoxy, a substituent is preferably the methoxy group.

Halogen atoms to be emphasised as substituents $R_1$, $R_2$, $R_3$ and $R_4$ are, in particular, fluorine and chlorine.

The stated substituents $R_1$, $R_2$ and $R_3$ are preferably in the o- and/or m-position. The substituent $R_4$ represents preferably a chlorine atom, and is preferably in the p-position to the anilino group.

The invention relates also to the salts of the compounds of formula I. For use as medicaments, such salts are preferred which are pharmaceutically acceptable. By this are meant, in particular, salts with bases of which the cations, in the case of the dosages in have either no inherent pharmacological action or a desired one. It is moreover of advantage if the salts to be used as active substances crystallise well and are not, or only slightly, hygroscopic. For salt formation with compounds of formula I it is possible to use, for example, inorganic bases such as, e.g. aqueous or aqueous-alcoholic solutions of alkali metal hydroxides or alkaline-earth metal hydroxides.

The compounds of the present invention possess valuable pharmacological properties. They thus ixhibit plateletaggregation and exhibit antiphlogistic (antiinflammatory), analgesic and antipyretic activity, which can be shown in tests on animals, e.g. in the case of oral administration in dosages of about 3 to 50 mg/kg to the mouse. Furthermore, the compounds are distinguished by a relatively low toxicity and good gastrointestinal compatibility, which can likewise be demonstrated in standard animal tests. For example, the analgesic activity of the new compounds of formula I in the case of oral administration to the mouse can be demonstrated using the method described by E. Siegmund, R. Cadmus and G. Lu, Proc. Soc. Exp. Biol. Med. 95, 729 (1957), whereby the amount of substance is determined which is required to prevent the syndrome produced by the intraperitoneal injection of 2-phenyl-1,4-benzoquinone. The antiphlogistic activity of substituted o-anilino-phenylacetohydroxamic acids of formula I can be shown, e.g. in the case of oral administration to the guinea pig in the UV-erythema test described by G. Wilhelmi, Schweiz. Med. Wochenschrift 79, 577 (1949); as well as on rats in the bolus alba oedema test according to G. Wilhelmi, Jap. J. Pharmacol. 15, 187 (1965). Mentioned as a further test for the antiphlogistic activity and the compatability is the cotton pellet granuloma test. In this test, each of a group of rats has implanted subcutaneously under the skin of the back, whilst the rat is under ether anaesthesia, two ca. 1 cm long cotton-wool pellets. The test substance is subsequently administered in equal dosages on 10 successive days. The animals are killed on the 11th day, the formed granulomas are peeled out and the wet and dry weight of them determined. The extent of granuloma inhibition is assessed from a comparison of the dry weights of the granulomas from rats which have received the test substance with the dry weights of the granulomas from the control animals. The increase in weight of the animals during the period of administration of the test substances is recorded as a measure of compatibility.

The gastrointestinal compatibility is determined, for example, by observation of the ulcerative action in the case of rats; the active substance is hereby administered twice orally at an interval of 15 hours, the animals are killed 21 hours after the first administration, and the condition of the digestive tracts is assessed on the basis of the number of ulcers formed and further changes on the mucous membrane.

The antipyretic action was determined by administration orally of compounds of the general formula I, in suitable dosage amounts, to groups of rats which had been injected intramuscularly, 16 to 18 hours previously, with a suspension of 15% of baker's yeast with 1% of tragacanth and 1% of sodium chloride in distilled water, in an amount of 1 ml per 100 g of body weight. The fever temperatures produced by the yeast were measured rectally at intervals of half an hour, i.e. one hour and half an hour before administration of the test substances and over the period extending from half an hour to 5 hours after administration of the test substances; by this means were obtained the maximum temperature fall and the arithmetical mean temperature fall during the 5 hours after administration of the test substances; this value was then compared with the average value of the two readings taken before administration to thus obtain a basis of comparison.

The Inhibition of plateletaggregation can be shown in vitro and in vivo by known methods, f.i. as described by J. T. Mustard et al., J. Lab. and Clinical Medicine 64, 548 (1964) and G. V. R. Born, Nature (London) 194, 927 (1962).

The compounds of formula I absorb ultraviolet light of the wave-length range of approximately 290 to about 315 m$\mu$. This special property makes these substances particularly suitable for incorporation into cosmetic preparations for the prevention of sun-burn. With a suitable composition of such sun-ray filter preparations, sun-burn is avoided by application of the said preparations without, however, the desired browning of the skin being prevented. An advantage of the claimed compounds is, that they can be made perceptible by a spot test in extremely small amounts on human skin by very diluted solutions of ferrichloride. By the intensive red-brown colour of the Fe-complex it is possible to control the presence of a protective amount of a claimed compound on human skin. A similar simple and safe test is not known for other sunburn protective agents, especially not for the corresponding carboxylic acids. The ferric chloride that is used for this purpose is absolutely nonpoisonous and is used, moreover, even in sporting activities, for preventing minor wounds (abrasions, cuts, nose bleeds) from bleeding. A similar expedient and non-poisonous method for detecting the active substance in applied sunray filter preparations has not become known up till now.

The carboxylic acids that correspond to the instant hydroxamic acids are labile because they pass over into the corresponding oxindole through intramolecular cyclisation accompanied by splitting off of water. This conversion into the oxindole can also occur with the hydroxamic acids of the instant invention. But comparison tests have shown that, in the case of the hydroxamic acids, this conversion (instability) proceeds about 7 to 11 times more slowly than in that of the corresponding carboxylic acids. The conversion into the oxindole of both the carboxylic and hydroxamic acids in aqueous medium can be accelerated by lowering the pH. This instability can therefore matter to a certain extent with compounds that are administered orally, because the gastric juice has a pH of about 2.

The new substituted o-anilino-phenylacetohydroxamic acids of formula I are suitable as active substances for medicaments administered orally, rectally, parenterally or percutaneously for the relief and removal of pains and inflammation of varying origin, e.g. of post-traumatic and postoperative nature, and for medicaments which can be administered orally, rectally, parenterally or percutaneously for the treatment of rheumatic, arthritic and other inflammatory diseases.

Particularly worthy of mention are compounds of formula Ia:

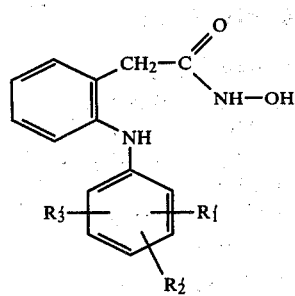

wherein $R_1'$ represents hydrogen, methyl, or halogen up to and including atomic number 35, $R_2'$ represents hydrogen, methyl, halogen up to and including atomic number 35, or trifluoromethyl, and $R_3'$ represents hydrogen, methyl, or halogen up to and including atomic number 35, with exclusion of the simultaneous definition of $R_1'$, $R_2'$ and $R_3'$ as hydrogen, and salts of such compounds.

Especially preferred are compounds of formula Ib:

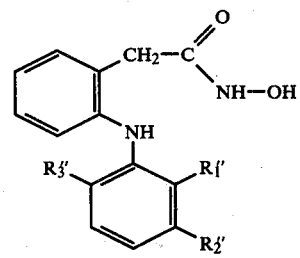

wherein $R_1''$ represents methyl or chlorine, $R_2''$ represents hydrogen, methyl or chlorine, and $R_3''$ represents hydrogen, methyl or chlorine, and salts thereof.

The following are to be emphasised by virtue of their particularly favourable pharmacological properties:

[o-(2,6-dichloroanilino)-phenyl]-acetohydroxamic acid.

[o-(2,6-dichloro-m-toluidino)-phenyl]-acetohydroxamic acid,

[o-(3-chloro-o-toluidino)-phenyl]-acetohydroxamic acid,

[o-(6-chloro-o-toluidino)-phenyl]-acetohydroxamic acid, and

[o-(2,6-xylidino)-phenyl]-acetohydroxamic acid

The new compounds of formula I and their salts are produced in a manner known per se.

By application of the process according to the invention, compounds of formula I and their salts with inorganic bases are produced by the reaction of an amide or an ester of an acid of formula II:

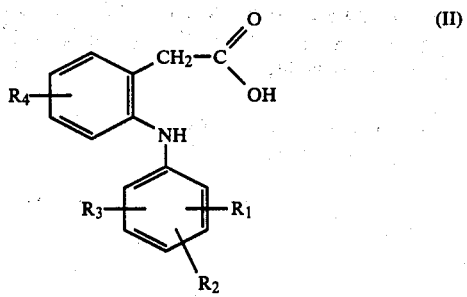

wherein $R_1$, $R_2$, $R_3$ and $R_4$ have the meanings given under formula I with hydroxylamine or a salt thereof in a basic medium, and, optionally, conversion of an obtained compound of the formula I into a salt with an inorganic base.

As amides of an acid of formula II are preferably used compounds unsubstituted on the amide nitrogen atom. As esters of an acid of formula II are preferably used lower alkyl esters. As activated ester can be used, e.g. the p-nitrobenzyl, the ethoxycarbonylmethyl, the methoxymethyl, the p-nitrothiophenyl esters and, preferably, the cyanomethyl, or the p-nitrophenyl esters of acids of formula II.

The reaction is performed in an organic solvent, preferably at a temperature of between 20° and 100° C. or at the boiling temperature of the applied solvent, and with a reaction time of between 20 minutes and 15 hours.

As suitable solvents are used organic solvents inert under the reaction conditions, such as, e.g. lower alkanols, acetonitrile or chloroform. It is moreover possible to use acetone, diethyl ether, di-n-butyl ether, ethyl acetate, 1,2-dichloroethane, dimethylformamide, dimethylsulphoxide, 1,4-dioxane, methylene chloride, nitromethane, petroleum ether, tetrachloroethylene, carbon tetrachloride or trichloroethylene, as well as benzene, nitrobenzene, pyridine or toluene.

The choice of the advantageous solvent in the individual case is also governed by the nature of the particular starting materials used. For example, the reaction of a lower alkyl ester or amide of an acid of formula II is performed in a lower alkanol, preferably in methanol. As solvent in the case of the reaction of an activated ester of formula II are used, e.g. acetonitrile, chloroform, dimethylformamide or ethyl acetate.

The stated amides and esters of acids of formula II are reacted with hydroxylamine, or with a salt thereof, in stoichiometrical amounts, or with a hydroxylamine excess. With the reaction of the mentioned acid derivatives with hydroxylamine hydrochloride, a stronger base in comparison with the hydroxylamine has to be added in excess.

In the case of the reaction of lower alkyl esters or amides of acids of formula II, an addition is made to the reaction mixture of a base in an amount equivalent to the hydroxylamine hydrochloride, preferably, however, in an amount constituting a four-fold excess, examples of the base being, e.g. sodium alcoholate or alcoholic sodium hydroxide solution.

If activated esters, such as, e.g. the cyanomethyl ester or the p-nitrophenyl ester of an acid of formula II, are reacted, then an amount at least doubly equivalent to the hydroxylamine hydrochloride is added of a tertiary organic base, such as, e.g. triethylamine or pyridine.

Some examples of the lower alkyl esters and amides of an acid of formula II are known, and others can be produced analogously to the known examples. Lower alkyl esters are produced, e.g. by esterification of the corresponding acids of formula II, or by alcoholysis of the corresponding nitriles. From the obtained lower alkyl esters are obtained in a known manner, after reaction with ammonia, the corresponding amides.

The substituted o-anilino-phenylacetic acid-cyanomethyl esters are produced from the corresponding substituted o-anilino-phenylacetic acids of formula II by reaction with chloroacetonitrile in the presence of the equivalent amount of triethylamine, or by reaction of the Na-salts of the stated acids with chloroacetonitrile in a suitable solvent, such as dimethylsulphoxide; obtained in an analogous manner are the substituted o-anilino-phenylacetic acid-p-nitrobenzyl esters, -ethoxycarbonylmethyl esters and -methoxymethyl esters. The substituted p-nitrophenyl esters of acids of formula II are obtained from the corresponding acids by reaction with trifluoroacetic acid-p-nitrophenyl ester in the presence of pyridine; obtained analogously is also p-nitrothiophenyl ester.

Optionally, the new phenylacetohydroxamic acids of formula I produced by the process according to the invention are converted, in the usual manner, into their salts with inorganic bases.

For salt formation with compounds of formula I it is possible to use, for example, alkali metal hydroxides such as, e.g. sodium or potassium hydroxide, or alkaline-earth metal hydroxides such as, e.g. calcium hydroxide.

The substituted phenylacetohydroxamic acids of the general formula I can be administered orally, rectally or parenterally. They may also be used externally, e.g. incorporated into ointment bases.

Medicaments according to the invention which are used for the above mentioned applications contain, as active substances, at least one compound of formula I in combination with an inert carrier and, optionally, further additives. The medicaments according to the invention preferably consist of dosage units suitable for the oral, rectal or parenteral administration of daily dosages of between 3 and 50 mg/kg of the active substance to warm-blooded animals. Suitable dosage units for oral, rectal or parenteral administration, such as dragees, tablets, capsules, suppositories or ampoules, contain as active substance preferably 25-500 mg of a compound of formula I.

In the dosage units for oral administration, the content of active substance preferably amounts to between 10% and 90%. Tablets or dragée-cores are produced by the combination of the active substances, e.g. with solid pulverulent carriers such as lactose, saccharose, sorbitol, mannitol; starches such as potato starch, maize starch or amylopectin, also laminaria powder or citrus pulp powder; cellulose derivatives or gelatine, optionally with the addition of lubricants such as magnesium stearate or calcium stearate, or polyethylene glycols, to form tablets or dragée cores. The last-mentioned are coated, e.g. with concentrated sugar solutions which can also contain, e.g. gum arabic, talcum and/or titanium dioxide; or with a lacquer dissolved in readily volatile organic solvents or solvent mixtures. Dyestuffs can be added to these coatings, e.g. for identification of the various dosages of active substance. Further suitable oral dosage units are hard gelatine capsules the outer covering of which contains gelatine, glycerin and water; as well as soft closed capsules having an outer covering which likewise contains gelatine, glycerin and water, but in a different mixture ratio. The hard capsules contain the active substances preferably as a granulate in admixture with lubricants such as talcum or magnesium stearate, and optionally stabilisers such as sodium metabisulphite ($Na_2S_2O_5$), or ascorbic acid. In soft capsules, however, the active substance is preferably dissolved or suspended in suitable liquids, such as in liquid polyethylene glycols, whereby likewise stabilisers may be added.

Ampoule solutions for administration parenterally, especially intramuscularly, also intravenously, contain a compound of the general formula I in a concentration of preferably 0.5–5%. They are produced with the aid of polar solvents, e.g. lower alkanols, alkanepolyols or partial ethers of the latter, such as ethanol or 1,2-propanediol, or 1-methoxy-2-propanol, or 2-ethoxyethanol, and water the proportion of which is preferably between 20% and 60%.

The following instructions further illustrate the production of various preparations:

(a) An amount of 500 g of active substance, e.g. [o-(2,6-dichloroanilino)-phenyl]-acetohydroxamic acid, is mixed with 550 g of lactose and 292 g of potato starch; the mixture is moistened with an alcoholic solution of 8 g of gelatine, and then granulated through a sieve. After drying of the granulate, 60 g of potato starch, 60 g of talcum, and 10 g magnesium stearate, and 20 g of highly dispersed silicon dioxide are mixed in, and the mixture is pressed out to obtain 10,000 tablets each weighing 150 mg and each containing 50 mg of active substance. Optionally, the tablets can be provided with grooves to ensure a more precise adjustment of the dosage amount.

(b) An amount of 50 g of active substance, e.g. [o-(2,6-dichloroanilino)-phenyl]-acetohydroxamic acid, is well mixed with 16 g of maize starch amd 6 g of highly dispersed silicon dioxide; the mixture is moistened with a solution of 2 g of stearic acid, 6 g of ethyl cellulose and 6 g of stearin in ca. 70 ml of isopropyl alcohol, and then granulated through a sieve III (Pharm.Helv.Ed.V). The granulate is dried for ca. 14 hours, and then put through a sieve III-IIIa; the sieved granulate is thereupon mixed with 16 g of maize starch, 16 g of talcum and 2 g of magnesium stearate, and the mixture pressed out to form 1,000 dagrée cores. These are coated with a concentrated syrup of 2 g of lacca, 7.5 g of gum arabic, 0.15 g of dyestuff, 2 g of highly dispersed silicon dioxide, 25 g of talcum, and 53.35 g of sugar; the coated dragée cores are then dried. The obtained dragées each weigh 210 mg and each contain 50 mg of active substance.

(c) To obtain 1,000 capsules each containing 75 mg of active substance, 75.0 g of [o-(3-chloro-o-toluidino)-phenyl]-acetohydroxamic acid are mixed with 198.0 g of lactose; the mixture is uniformly moistened with an aqueous solution of 2.0 g of gelatine, and then granulated through a suitable sieve (e.g. sieve III according to Ph.Helv.V). The granulate is mixed with 10.0 g of dried maize starch and 15.0 g of talcum, and the mixture evenly filled into 1,000 hard gelatine capsules, size 1.

(d) 50 g of [o-(6-chloro-o-toluidino)-phenyl]-acetohydroxamic acid and 1,950 g of finely ground suppository base (e.g. cocoa butter) are thoroughly mixed and then melted. From the melt, maintained homogeneous by stirring, are poured 1,000 suppositories each weighing 2 g; they each contain 50 g of active substance.

(e) An amount of 5 g of [o-(2,6-dichloroanilino)-phenyl]-acetohydroxamic acid is dissolved in 60 g of 1-methoxy-2-propanol, and the solution made up to 100 ml with sterile distilled water; the solution is then filtered and poured into ampoules, each containing, e.g. 1 ml, corresponding to a content of 50 mg of active substance. The filled ampoules are sterilised in the heat as usual.

(f) The following recipe can, for example, be used for the preparation of ointments:

| | |
|---|---|
| [o-(2,6-dichloroanilino)-phenyl]-acetohydroxamic acid | 1.0 g |
| propylene glycol | 28.0 g |
| glycerin monostearate | 18.0 g |
| polyoxyethylene-sorbitan-monolaurate | 8.0 g |
| thimerosal (solution 1 : 1,000) | 1.0 g |
| perfume | q.s. |
| water | ad 100.0 g |

The following examples further illustrate the carrying out of the process according to the invention; these examples, however, in no way limit the scope of the invention. The temperatures are given in degrees Centigrade.

EXAMPLE 1

[o-(2,6-dichloroanilino)-phenyl]-acetohydroxamic acid

To a solution of 18.7 g of sodium in 400 ml of abs. methanol is added, at room temperature, a solution of 17.5 g of hydroxylamine hydrochloride in 260 ml of abs. methanol. To the suspension are added, with stirring, 77.6 g of [o-(2,6-dichloroanilino)-phenyl]-acetic acid methyl ester (M.P. 101°–102°), and the whole is then refluxed for 30 minutes. The mixture is cooled, and concentrated at 40° under 11 Torr to dryness. To the residue are added 4,000 ml of water and 500 ml of ether; the mixture is stirred for 20 minutes, the aqueous solution separated, and rendered acid with 5 N hydrochloric acid. The suspension is extracted with 2,000 ml of ether; the ether solution is then washed with 200 ml of water and 200 ml of saturated sodium chloride solution, dried over sodium sulphate, and concentrated at 40° under 11 Torr. The residue is crystallised twice from ethyl acetate/-petroleum ether. The obtained [o-(2,6-dichloroanilino)-phenyl]-acetohydroxamic acid melts at 164°–165°.

The following are obtained in an analogous manner:

[o-(2,6-dichloro-m-toluidino)-phenyl]-acetohydroxamic acid, M.P. 140°–145° (from ether/petroleum ether) starting from 16.2 g of [O-(2,6-dichloro-m-toluidino)-phenyl]-acetic acid methyl ester, M.P. 110°–112°;

[o-(6-chloro-o-toluidino)-phenyl]-acetohydroxamic acid, M.P. 159°–162° (from ethyl acetate/petroleum ether), starting with 29.1 g of [o-(6-chloro-o-toluidino)-phenyl]-acetic acid methyl ester, M.P. 99°–100° (from cyclohexane);

[o-(2,6-xylidino)-phenyl]-acetohydroxamic acid, M.P. 134°–136° (from ethyl acetate/petroleum ether), starting with 4.9 g of [o-(2,6-xylidino)-phenyl]-acetic acid methyl ester, M.P. 79°–80° (from ether/petroleum ether);

[o-(3-chloro-o-toluidino)-phenyl]-acetohydroxamic acid, M.P. 135°–136° (from ether/petroleum ether), starting with 7.2 g of [o-(3-chloro-o-toluidino)-phenyl]-acetic acid methyl ester, M.P. 47°–48°) from ether/petroleum ether).

[o-(3-chloro-o-toluidino)-phenyl]acetic acid methyl ester is obtained, for example, as follows:

(a) N-(3-chloro-o-tolyl)-anthranilic acid

A mixture of 665 g of o-bromobenzoic acid and 220 g of 85% potassium hydroxide in 1,800 ml of n-pentanol is heated to 160° whilst stirring is maintained. Within 30 minutes, ca. 400 ml of n-pentanol are distilled off. To the mixture are then added 940 g of 3-chloro-o-toluidine and 12.5 g of copper powder, and the mixture is refluxed for 15 hours. It is afterwards cooled and then poured into a solution of 180 g of sodium carbonate in 600 ml of water, and the solution distilled with steam. After the excess 3-chloro-o-toluidine has been distilled off, the aqueous residue is filtered, and the filtrate acidified with concentrated hydrochloric acid. The precipitated crystals are filtered off, and crystallised from ethanol/water. Thus obtained is N-(3-chlorotolyl)-anthanilic acid, M.P. 212°–215°.

(b) N-phenyl-3-chloro-o-toluidine

An amount of 150 g of N-(3-chloro-o-tolyl)-anthranilic acid is heated to 280° for 2½ hours. The cooled melt is dissolved in 700 ml of ether; the ether solution is then washed twice with 150 ml of 2 N sodium carbonate solution and 150 ml of water. The ether solution is afterwards separated, dried over sodium sulphate, and concentrated at 40° under 11 Torr to dryness. The residue is distilled, whereby N-phenyl-3-chloro-o-toluidine is obtained as yellow oil, B.P. 117°/0.01 Torr.

(c) N-phenyl-3'-chloro-2'-methyl-oxaniloyl chloride

To a solution of 94.5 g of N-phenyl-3-chloro-o-toluidine in 560 ml of anhydrous benzene is slowly added dropwise, at 5°, 137 ml of oxalyl chloride. The suspension is then stirred for 2 hours at room temperature and for ½ hour at 50°, whereby the suspension goes into solution. The reaction solution is cooled, and concentrated to dryness under 11 Torr with a bath temperature of 40°. The residue is dissolved in 400 ml of anhydrous benzene, and the solution again concentrated to dryness under 11 Torr. The residue: N-phenyl-3'-chloro-2'-methyloxaniloyl chloride, is obtained as oil.

(d) 1-(3-chloro-o-tolyl)-indole-2,3-dione

To a solution of 134 g of N-phenyl-3'-chloro-2'-methyloxaniloyl chloride in 900 ml of tetrachloroethane are added in portions 58.6 g of powdered aluminium chloride. The mixture is stirred for 20 hours at room temperature; it is then poured on to a mixture of 2,000 g of ice and 200 ml of 2 N hydrochloric acid; an amount of 500 ml of chloroform is added and the whole well shaken. The tetrachloroethane/chloroform solution is separated, washed with 300 ml of 2 N sodium carbonate solution, and afterwards with 300 ml of water; the solution is then dried over sodium sulphate, and concentrated under 0.1 Torr to dryness. The residue is crystallised from ethyl acetate. The obtained 1-(3-chloro-o-tolyl)-indole-2,3-dione melts at 173°–174°.

(e) Sodium salt of [o-(3-chloro-o-toluidino)-phenyl]-glyoxylic acid

A solution of 57 g of 1-(3-chloro-o-tolyl)-indole-2,3-dione in 800 ml of ethanol and 210 ml of 1 N sodium hydroxide solution is concentrated to dryness at 40° under 11 Torr. To the residue are added 100 ml of abs. benzene twice, and each time the mixture is concentrated to dryness at 40° under 11 Torr, whereupon pure sodium salt of [o-(3-chloro-o-toluidino)-phenyl]-glyoxylic acid is obtained.

(f) [o-(3-chloro-o-toluidino)-phenyl]-acetic acid

To a solution of 35.5 g of sodium salt of [o-(3-chloro-o-toluidino)-phenyl]-glyoxylic acid in 455 ml of abs. ethanol are added at 50° 28.5 g of hydrazine hydrate, and 5 minutes afterwards 66.2 g of sodium methylate. The solution is thereupon heated in an oil bath with a bath temperature of 150°, whereby the ethanol slowly distills off. To the solution are simultaneously added dropwise 455 ml of ethylene glycol monoethyl ether. The internal temperature thereby increases to 130°. After the dropwise addition is completed, the solution is stirred for a further hour at 150°; it is then cooled and diluted with 3,000 ml of water. The solution is extracted twice with 300 ml of ether each time, and then acidified with concentrated hydrochloric acid. The precipitated yellow oil is extracted with 200 ml of ethyl acetate; the ethyl acetate solution is washed with 200 ml of water, dried over sodium sulphate, and concentrated at 30° under 11 Torr, whereby [o-(3-chloro-o-toluidino)-phenyl]-acetic acid crystallises out, M.P. 124°–125°.

(g) [o-(3-chloro-o-toluidino)-phenyl]-acetic acid methyl ester

To a solution of 10 g of [o-(3-chloro-o-toluidino)-phenyl]-acetic acid (M.P. 124°–125°) in 100 ml of ether are slowly added dropwise 100 ml of 2% ethereal diazomethane solution. The solution is allowed to stand for 2 hours at room temperature, and then concentrated to dryness at 40° under 11 Torr. The residue is dissolved in 100 ml of ether. The ether solution is extracted with 40 ml of 2 N sodium hydrogen carbonate solution and water, dried over sodium sulphate, and concentrated at 40° under 11 Torr. The residue is crystallised from benzine. The obtained [o-(3-chloro-o-toluidino)-phenyl]-acetic acid methyl ester melts at 47°–48°.

EXAMPLE 2

[o-(2,6-dichloroanilino)-phenyl]-acetohydroxamic acid

To a mixture of 6.7 g of [o-(2,6-dichloroanilino)-phenyl]-acetic acid cyanomethyl ester (M.P. 100°–104°) and 0.7 g of hydroxylamine hydrochloride in 27 ml of acetonitrile are added 3 drops of glacial acetic acid and 1.01 g of triethylamine. The mixture is stirred for 30 minutes at room temperature; to it are then added a further 0.35 g of hydroxylamine hydrochloride and 0.5 g of triethylamine, and stirring is continued for a further 15 hours at room temperature. The mixture is thereupon concentrated at 50° under 11 Torr. To the residue are added 30 ml of water and 100 ml of ethyl acetate. The ethyl acetate solution is separated and concentrated under 11 Torr. The residue is dissolved in 100 ml of ether, and the ether solution extracted with 10 ml of 1 N sodium hydroxide solution, whereby [o-(2,6-dichloroanilino)-phenyl]-acetohydroxamic acid-Na-salt precipitates in crystalline form. The crystals are filtered off, suspended in 50 ml of ether, and the suspension is shaken with 20 ml of 6 N hydrochloric acid. The clear ether phase is separated, dried over sodium sulphate, and concentrated at 40° under 11 Torr. The residue is crystallised from ether. The obtained [o-(2,6-dichloroanilino)-phenyl]-acetohydroxamic acid melts at 164°–165°.

The following are obtained analogously:

[o-(2,6-dichloro-m-toluidino)-phenyl]-acetohydroxamic acid, M.P. 140°–145° (from ether/petroleum ether), starting with [o-(2,6-dichloro-m-toluidino)-phenyl]-acetic acid cyanomethyl ester;

[o-(6-chloro-o-toluidino)-phenyl]-acetohydroxamic acid, M.P. 159°–162° (from ethyl acetate/petroleum ether), starting with [o-(6-chloro-o-toluidino)-phenyl]-acetic acid cyanomethyl ester;

[o-(2,6-xylidino)-phenyl]-acetohydroxamic acid, M.P. 134°–136° (from ethyl acetate/petroleum ether), starting with [o-(2,6-xylidino)-phenyl]-acetic acid cyanomethyl ester;

[o-(3-chloro-o-toluidino)-phenyl]-acetohydroxamic acid, M.P. 135°–136° (from ether/petroleum ether), starting with [o-(3-chloro-o-toluidino)-phenyl]-acetic acid cyanomethyl ester.

The starting materials are obtained as follows:

(a) [o-(2,6-dichloroanilino)-phenyl]-acetic acid cyanomethyl ester

A mixture of 2.96 g of [o-(2,6-dichloroanilino)-phenyl]-acetic acid (M.P. 156°–158° from ether/petroleum ether), 1.13 g of chloroacetonitrile and 1.51 g of triethylamine in 30 ml of ethyl acetate is stirred for 15 hours at 60°; the mixture is then cooled and separated from the precipitated triethylamine hydrochloride. The filtrate is washed with 5 ml of 1 N hydrochloric acid, three times with 5 ml of sodium hydrogen carbonate solution each time, as well as with 5 ml of water; it is afterwards dried over sodium sulphate, and concentrated at 50° under 11 Torr. The residue is crystallised from methanol. The obtained [o-(2,6-dichloroanilino)-phenyl]-acetic acid cyanomethyl ester melts at 100°–104°.

The following are obtained analogously:

[o-(2,6-dichloro-m-toluidino)-phenyl]-acetic acid cyanomethyl ester starting with [o-(2,6-dichloro-m-toluidino)-phenyl]-acetic acid, M.P. 146°–149° (from ether/petroleum ether);

[o-(6-chloro-o-toluidino)-phenyl]-acetic acid cyanomethyl ester, starting with [o-(6-chloro-o-toluidino)-phenyl]-acetic acid, M.P. 140°–147° (from ether/petroleum ether);

[o-(2,6-xylidino)-phenyl]-acetic acid cyanomethyl ester, starting with [o-(2,6-xylidino)-phenyl]-acetic acid, M.P. 112°–113° (from ether/petroleum ether);

[o-(3-chloro-2-methyl)-phenyl]-acetic acid cyanomethyl ester, starting with [o-(3-chloro-o-toluidino)-phenyl]-acetic acid, M.P. 124°–125° (from ether/petroleum ether).

(b) [o-(2,6-dichloroanilino)-phenyl]-acetic acid cyanomethyl ester

To a solution of 5.0 g of [o-(2,6-dichloroanilino)-phenyl]-acetic acid-Na-salt (M.P. 283°–285° from water) in 30 ml of dimethylsulphoxide are added, at room temperature, 30 ml of chloroacetonitrile. The mixture is stirred for 20 minutes at room temperature; it is then poured on 100 g of ice and extracted with 200 ml of ether. The ether solution is washed with 30 ml of 2 N potassium hydrogen carbonate solution, and three times with 30 ml of water each time; it is then dried over sodium sulphate and concentrated at 40° under 11 Torr. The residue is crystallised from methanol. The obtained [o-(2,6-dichloroanilino)-phenyl]-acetic acid cyanomethyl ester melts at 100°–104°.

The following are obtained analogously:

[o-(2,6-dichloro-m-toluidino)-phenyl]-acetic acid cyanomethyl ester starting with [o-(2,6-dichloro-m-toluidino)-phenyl]-acetic acid-Na-salt, M.P. 287°–289° (from water);

[o-(6-chloro-o-toluidino)-phenyl]-acetic acid cyanomethyl ester, starting with [o-(6-chloro-o-toluidino)-phenyl]-acetic acid-K-salt, M.P. 285°–300° (decomposition from methanol);

[o-(2,6-xylidino)-phenyl]-acetic acid cyanomethyl ester, starting with [o-(2,6-xylidino)-phenyl]-acetic acid-Na-salt, M.P. 298°–305° (from water).

EXAMPLE 3

[o-(2,6-dichloroanilino)-phenyl]-acetohydroxamic acid

An amount of 2.76 g of triethylamine is added, at room temperature, to a suspension of 4.17 g of [o-(2,6-dichloroanilino)-phenyl]-acetic acid-p-nitrophenyl ester (M.P. 105°–106°) and 0.69 g of hydroxylamine hydrochloride in 50 ml of abs. chloroform. The clear solution is stirred for 30 minutes at room temperature and then concentrated under 11 Torr to dryness. To the residue are added 100 ml of ether and 5 ml of 2 N hydrochloric acid. The ether solution is separated, washed twice with 40 ml of water each time, dried over sodium sulphate, and concentrated at 40° under 11 Torr. The residue is crystallised from ether. The obtained [o-(2,6-dichloroanilino)-phenyl]-acetohydroxamic acid melts at 164°–165°.

The following is obtained analogously:

[o-(3-chloro-o-toluidino)-phenyl]-acetohydroxamic acid, M.P. 135°–136° (from ether/petroleum ether), starting with [o-(3-chloro-o-toluidino)-phenyl]-acetic acid-p-nitrophenyl ester.

The starting material is obtained as follows:

[o-(2,6-dichloroanilino)-phenyl]-acetic acid-p-nitrophenyl ester

To a solution of 6.0 g of [o-(2,6-dichloroanilino)-phenyl]-acetic acid in 20 ml of pyridine are added in portions, with stirring, 6.0 g of trifluoroacetic acid-p-nitrophenyl ester (produced according to S. Sakakibara and N. Inakai, Bull.Chem.Soc.Jap. 1983 [1965]). The mixture is stirred for one hour at room temperature, and then concentrated at 30°–40° under 11 Torr. To the residue are added 20 ml of water and extraction is carried out with 50 ml of chloroform. The aqueous phase is separated, and again extracted with a further 30 ml of chloroform. Then combined chloroform solutions are extracted with 20 ml of 1 N hydrochloric acid, 20 ml of 1 N potassium hydrogen carbonate solution, and twice with 20 ml of water each time, separated, dried over sodium sulphate, and concentrated under 11 Torr. The residue is crystallised from methanol. The obtained [o-(2,6-dichloroanilino)-phenyl]-acetic acid-p-nitrophenyl ester melts at 105°–106°.

The following is obtained analogously:

[o-(3-chloro-o-toluidino)-phenyl]-acetic acid-p-nitrophenyl ester, starting with [o-(3-chloro-o-toluidino)-phenyl]-acetic acid, M.P. 124°–125° (from ether/petroleum ether).

EXAMPLE 4

[o-(2,6-dichloroanilino)-phenyl]-acetohydroxamic acid

To a solution of 1.84 g of sodium in 80 ml of methanol is added, at 50°, a solution of 1.82 g of hydroxylamine hydrochloride in 30 ml of methanol. To the suspension is added, with stirring, a solution of 5.8 g of [o-(2,6- dichloroanilino)-phenyl]-acetamide (M.P. 188°–189°) in 80 ml of methanol, and the whole subsequently refluxed for 18 hours. After cooling, the red suspension is concentrated at 40° under 11 Torr to dryness. The residue is shaken with 600 ml of water and 100 ml of ether. The aqueous phase is separated and acidified with 2 N hydrochloric acid. The suspension is extracted with 200 ml of ether, the ether solution separated, washed with water, dried over magnesium sulphate, and concentrated at 40° under 11 Torr. The residue is crystallized from ether, whereby [o-(2,6-dichloroanilino)-phenyl]-acetohydroxamic acid is obtained, M.P. 164°–165°.

The following are obtained analogously:

[o-(3-chloro-o-toluidino)-phenyl]-acetohydroxamic acid, M.P. 135°–136° (from ether/petroleum ether), starting with 4.2 g of [o-(3-chloro-o-toluidino)-phenyl]-acetamide, M.P. 139°–141° (from ether/petroleum ether);

[o-(2,6-dichloro-m-toluidino)-phenyl]-acetohydroxamic acid, M.P. 140°–145°, starting with [o-(2,6-dichloro-m-toluidino)-phenyl]-acetamide;

[o-(6-chloro-o-toluidino)-phenyl]-acetohydroxamic acid, M.P. 159°–162°, starting with [o-(6-chloro-o-toluidino)-phenyl]-acetamide, M.P. 166°–168°;

[o-(2,6-xylidino)-phenyl]-acetohydroxamic acid, M.P. 134°–136°, starting with [o-(2,6-xylidino)-phenyl]-acetamide.

The starting material is obtained as follows:

[o-(3-chloro-o-toluidino)-phenyl]-acetamide

A mixture of 7.8 g of [o-(3-chloro-o-toluidino)-phenyl]-acetic acid methyl ester (M.P. 47°–48°) and 100 ml of liquid ammonia is stirred for 4 days at room temperature in an autoclave. The ammonia is thereupon evaporated off and the residue chromatographed on 240 g of neutral aluminium oxide. The fractions 1–15 eluted with ether/chloroform 1:1 contain N-(3-chloro-o-tolyl)-indolinone; the fractions 16–22 eluted with chloroform/methanol 99:1 contain [o-(3-chloro-o-toluidino)-phenyl]-acetamide, M.P. 139°–141° (from ether/petroleum ether).

What is claimed is:

1. A compound of the formula

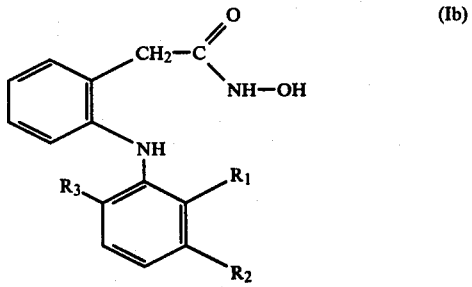

wherein $R_1$ is methyl or chlorine and each of $R_2$ and $R_3$ is hydrogen, methyl or chlorine; or an alkali metal or alkaline earth metal salt thereof.

2. A compound according to claim 1 which is the [o-(2,6-dichloroanilino)-phenyl]-acetohydroxamic acid.

3. A compound according to claim 1 which is the [o-(3-chloro-o-toluidino)-phenyl]-acetohydroxamic acid.

* * * * *